(12) United States Patent
Paige et al.

(10) Patent No.: US 7,710,568 B1
(45) Date of Patent: *May 4, 2010

(54) PORTABLE NATURAL GAS LEAK DETECTOR

(75) Inventors: Mark E. Paige, Santa Fe, NM (US);
Joel A. Silver, Santa Fe, NM (US);
Frank T. Petroski, Jr., Norcross, GA (US); Sean Durkin, Suwanee, GA (US)

(73) Assignees: Southwest Sciences Incorporated, Sante Fe, NM (US); Southern Cross Corporation, Norcross, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/238,819

(22) Filed: Sep. 26, 2008

Related U.S. Application Data

(60) Provisional application No. 60/976,068, filed on Sep. 28, 2007.

(51) Int. Cl.
*G01N 21/00* (2006.01)
(52) U.S. Cl. .......................... 356/437; 356/73; 356/328
(58) Field of Classification Search ................. 356/244, 356/246, 432–444, 72–73, 326, 328; 250/343, 250/576, 372, 461.1, 339.08
See application file for complete search history.

(56) References Cited

U.S. PATENT DOCUMENTS

| | | | | |
|---|---|---|---|---|
| 4,160,373 A * | 7/1979 | Fastaia et al. | ............... | 73/23.31 |
| 4,297,035 A | 10/1981 | Bjorklund | | |
| 4,507,558 A | 3/1985 | Bonne | | |
| 4,520,265 A | 5/1985 | Griggs et al. | | |
| 4,765,736 A | 8/1988 | Gallagher et al. | | |
| 4,934,816 A | 6/1990 | Silver et al. | | |
| 5,055,690 A * | 10/1991 | Bonne | ............... | 250/343 |
| 5,134,276 A | 7/1992 | Hobbs | | |
| 5,570,697 A * | 11/1996 | Walker et al. | ............... | 600/532 |
| 5,777,735 A * | 7/1998 | Reagen | ............... | 356/451 |
| 6,005,661 A | 12/1999 | Machler | | |
| 6,031,609 A | 2/2000 | Funk et al. | | |
| 6,091,504 A * | 7/2000 | Walker et al. | ............... | 356/437 |
| 6,188,474 B1 | 2/2001 | Dussault et al. | | |
| 6,201,245 B1 * | 3/2001 | Schrader | ............... | 250/349 |
| 6,643,016 B2 | 11/2003 | Garver et al. | | |
| 6,803,594 B2 * | 10/2004 | Spolaczyk et al. | ............... | 250/574 |
| 6,937,324 B2 * | 8/2005 | Kameoka | ............... | 356/73 |
| 7,075,653 B1 | 7/2006 | Rutherford | | |
| 7,134,999 B2 | 11/2006 | Brauker et al. | | |
| 7,236,243 B2 * | 6/2007 | Beecroft et al. | ............... | 356/328 |
| 7,288,770 B2 * | 10/2007 | Gamiles et al. | ............... | 250/372 |

(Continued)

OTHER PUBLICATIONS

"Product Detail—Flame Pack 300", http://www.southerncross.corp.com/Prod-73-1-11/FlamePack400.htm 2007.

(Continued)

*Primary Examiner*—Sang Nguyen
(74) *Attorney, Agent, or Firm*—Samantha A. Updegraff; Jeffrey D. Myers; Peacock Myers, P.C.

(57) ABSTRACT

The present invention is a portable gas leak detector preferably comprising a portable optical spectroscopy apparatus for measurement of gas concentration.

27 Claims, 4 Drawing Sheets

U.S. PATENT DOCUMENTS

| | | | |
|---|---|---|---|
| 7,300,408 B2 * | 11/2007 | Hancock et al. | 600/532 |
| 7,616,316 B1 | 11/2009 | Silver et al. | |
| 2003/0010941 A1 | 1/2003 | Spolaczyk et al. | |
| 2004/0065816 A1 | 4/2004 | Ye et al. | |
| 2005/0286054 A1 * | 12/2005 | Chen et al. | 356/437 |

OTHER PUBLICATIONS

Bjorklund, G. C. et al., "Frequency Modulation (FM) Spectroscopy", *Applied Physics B* vol. 32, Springer-Verlag 1983, 145-152.

Bomse, David S. et al., "Frequency Modulation and Wavelength Modulation Spectroscopies: Comparison of Experimental Methods Using a Lead-Salt Diode Laser", *Applied Optics*, vol. 31, No. 6 Feb. 20, 1992, 718-731.

Chen, Hui et al., "Near-infrared saturation spectroscopy of cesium molecules using a diode laser", *J. Opt. Soc. Am. B* vol. 23, No. 4 Apr. 2006, 723-726.

Cooper, D. E. et al., "Double Frequency Modulation Spectroscopy", *Appl. Opt.* vol. 24 1985, 1327-1333.

Drayson, S. R., "Rapid Computation of the Voigt Profile", *J. Quant. Spectrosc. Radiat. Transfer* vol. 16, Pergamon Press, Great Britain 1976, 611-614.

Frish, M.B. et al., "Standoff gas leak detectors based on tunable diode laser absorption spectroscopy", *SPIE Optics East* Boston, MA., Society of Photo-Optical Instrumentation Engineers Oct. 23, 2005.

Herriott, Donald R. et al., "Folded Optical Delay Lines", *Applied Optics*, vol. 4, No. 8 Aug. 1965, 883-889.

Herriott, D. et al., "Off-Axis Paths in Spherical Mirro Interferometers", *Applied Optics* vol. 3, No. 4 Apr. 1964, 523-526.

Hirschfield, T., "Dynamic range improvement in Fourier transform infrared spectroscopy", *J. Am. Chem. Soc.* vol. 50 1978, 1227-1228.

Hobbs, P.C. D. et al., "Ultrasensitive laser measurements without tears", *Appl. Opt.* vol. 36 1997, 903-920.

Hui, A. K. et al., "Rapid Computation of the Voigt and Complex Error Functions", *J. Quant. Spectrosc. Radiat. Transfer* vol. 19, Pergamon Press, Great Britain 1978, 509-516.

Paige, M.E. et al., "Portable natural gas leak detector for survey inspections", *Proc. of SPIE* vol. 6378 2006, 63780Z.

Press, William H. et al., *Numerical Recipes in C, the Art of Scientific Computing* Cambridge University Press 1992, 59-71.

Reid, J. et al., "Sensitive limits of a tunable diode laser spectrometer with application to the detection of NO2 at the 100-ppt level", *Appl. Opt.* vol. 19 1980, 3349-3354.

Rothman, L. S. et al., "The HITRAN 2004 molecular spectroscopic database", *Jounral of Quantitative Spectroscopy & Radiative Transfer* vol. 96, Elsevier 2005, 139-204.

Sanders, Scott T. et al., "Rapid temperature tuning of a 1.4-um diode laser with application to high-pressure H2) absorption spectroscopy", *Optics Letters* vol. 26, No. 20, Optical Society of America Oct. 15, 2001, 1568-1570.

Silver, Joel A., "Frequency-Modulation Spectroscopy for Trace Species Detection: Theory and Comparison Among Experimental Methods", *Applied. Optics*, vol. 31, No. 6 Feb. 20, 1992, 707-717.

Silver, J. A. et al., "Two-Tone Optical Heterodyne Spectroscopy Using Buried Double Heterostructure Lead-Salt Diode Lasers", *Appl. Opt.* vol. 27 1988, 4438-4444.

Svanberg, S. et al., "Saturation spectroscopy for optically thick atomic samples", *J. Opt. Soc. Am. B* vol. 4, No. 4, Optical Society of America Apr. 1987, 462-469.

White, John U., "Long Optical Paths of Large Aperture", *Journal Optical Society Am.*, vol. 32 May 1952, 285-288.

White, Barry, "The Use of Combination Oxygen and Combustible Gas Detectors", *OSHA Hazard Information Bulletin* Jan. 18, 1990.

Zondlo, M. A. et al., "VCSEL-based hygrometer for the High-performance Instrumented Airborne Platform for Environmental Research (HIAPER)", *American Chemical Society National Meeting, Paper No. 302, Analytical Chemistry, Analytical Chemistry in the Atmospheric Sciences* San Diego, California Mar. 14, 2005.

* cited by examiner

| Gas Mixture Composition | Recovery to Zero ppm (seconds) |
|---|---|
| 100% | 60 |
| 5% | 14 |
| 1000 ppm | 8 |
| 500 ppm | 6 |
| 1 ppm | 2 |

FIG. 2

| Gas Concentration | Φ (Gas Concentration) | Readout Resolution |
|---|---|---|
| 10% | 2% | 1% |
| 1% | 0% | 0.05% |
| 100 ppm | 5 ppm | 1 ppm |
| 10 ppm | 1.1 ppm | 1 ppm |

FIG. 4

PORTABLE NATURAL GAS LEAK DETECTOR

CROSS-REFERENCE TO RELATED APPLICATIONS

This application claims priority to and the benefit of the filing of U.S. Provisional Patent Application Ser. No. 60/976,068, entitled "Portable Natural Gas Leak Detector", filed on Sep. 28, 2007, and the specification thereof is incorporated herein by reference.

This application is related to U.S. patent application Ser. No. 11/679,608, entitled "Gas Measurement Over Extreme Dynamic Range of Concentrations", filed on Feb. 27, 2007.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to gas concentration measurement and more specifically to a portable detector that measures gas concentration.

2. Description of Related Art

Walking inspection surveys for finding natural gas leaks are currently performed with a surveyor moving at a normal gait while dragging a leak detector along the ground. The surveyor pauses to further investigate an area only if the instrument alarms. Often, a low ppm plume is the sole initial indication of a leak. Thus, a useful instrument for this particular application must respond within approximately one to two seconds, be sensitive to 1 ppm changes in ambient methane concentration, and not alarm falsely. Once a leak is located, an ideal instrument could measure up to pure gas levels in order to further quantify the magnitude of the leak and the urgency required for corrective action.

Typically, leak concentrations must exceed 500 ppm to be deemed worthy of being reported. Low weight, the ability to run for a full eight hour workday, and intrinsic safety are also desirable instrument characteristics for this specific application.

There is currently no single instrument that meets all of the criteria stated above. Typically, a combination of instruments is used to accomplish leak surveying. Specifically, no instrument responds rapidly, continuously draws samples, and measures from ambient methane levels (approximately 1.7 ppm) to pure gas. For example, flame ionization detectors, which are commonly used in walking area surveys to find leaking gas, typically can detect a maximum concentration of 5000 ppm. These detectors are not intrinsically safe since they use fuel mixtures composed with approximately 40% hydrogen gas and have an internal flame. For higher gas concentrations, a combustible gas indicator is typically used. These thermal conductivity sensors measure from the lower explosion limit (5% gas) to pure gas levels. They do not make continuous measurements and require hand aspiration with a squeeze bulb. OSHA has noted that combustible gas indicators give false readings in environments in which the oxygen content is below 10%. All conventional gas leak detectors are responsive to any hydrocarbon and are not selective to methane. Nonselective detection is problematic in areas where other hydrocarbons may be present.

An embodiment of the present invention meets all the requirements for natural gas leak surveying. It measures all methane levels from ambient concentration (approximately 1.7 ppm) to pure gas. One embodiment of the present invention is preferably selective to methane and detects no other hydrocarbons. In other words, other gases do not effect the measurement of methane when using this embodiment. The one second time response of this embodiment allows it to be used in rapid walking area surveys. Embodiments of this invention also use no consumables and is constructed to be intrinsically safe.

BRIEF SUMMARY OF THE INVENTION

An embodiment of the present invention comprises a portable optical spectroscopy apparatus for measurement of gas concentration. This apparatus preferably comprises a laser light source, a fixed length optical path receiving light from the light source and containing a gas to be detected, a detector receiving light at an end of the path, signal processing electronics for acquiring data from the detector, a microcontroller receiving said data from said signal processing electronics. In this embodiment, the apparatus is handheld, and can preferably be held with a single hand. The gas being measured is preferably methane.

In another embodiment of the present invention, the portable optical spectroscopy apparatus additionally comprises a beamsplitter, a sample container containing the gas, a detector receiving light from the sample container, and signal-processing electronics establishing linelocking and a comparative signal source of the absorption feature.

In yet another embodiment of the present invention, the fixed length optical path comprises a multiple pass optical cell. In this embodiment, a pump continuously pumps gas through the multiple pass optical cell. The cell preferably comprises two mirrors configured in a Herriott cell design.

In a further embodiment of the present invention, the light source of the portable optical spectroscopy apparatus comprises a diode laser. A display is optionally included for displaying data from the microcontroller. The display preferably switches between displaying data in PPM, percent LEL and percent gas. Alarms are included in this embodiment. The alarms are controlled by the microcontroller. A user button is optionally included for inputting options and modes.

In another embodiment of the present invention, the apparatus comprises a telescoping sample probe and is powered using batteries.

A method for measuring gas concentration comprises the steps of holding a portable optical spectroscopy apparatus in an area to be measured, preferably holding the apparatus in a single hand, emitting light from a laser light source attached to the apparatus, receiving light via a fixed length optical path from the source and containing a gas to be detected, receiving light via a detector at an end of the path, determining one or more gas concentrations via signal processing electronics connected to the detector, and reporting the gas concentration data to a microcontroller. The gas being measured is preferably methane.

The method preferably comprises employing a beamsplitter, a sample container containing the gas, a detector receiving light from the sample container, and signal-processing electronics to establish linelocking and a comparative signal source of the absorption feature.

The method optionally comprises a multiple pass optical cell. A diode laser is preferably used as the light source. The method further continuously pumps the gas to be detected through the multiple pass optical cell. In this embodiment, the multiple pass optical cell preferably comprises two mirrors configured in a Herriott cell design.

The method also preferably displays the gas concentration data, controls alarms via the microcontroller, performs a calibration, inputs options and modes via a user button, and telescopes a sample probe in the area to be measured.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 2 is a table showing recovery times back to zero ppm;

FIG. 4 is a table showing results from an accuracy evaluation of the preferred embodiment.

DETAILED DESCRIPTION OF THE INVENTION

The present invention is directed to a portable gas leak detector. In a preferred embodiment, the portable gas leak detector is a diode laser sensor that determines gas concentration, preferably methane concentration.

Figure 1:
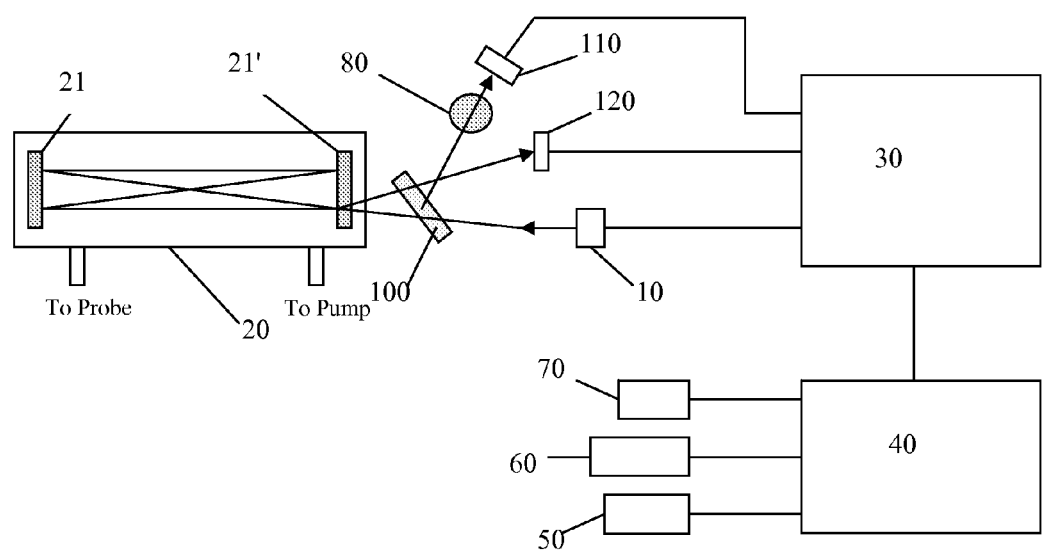
FIG. 1 is a preferred embodiment of the invention.

A schematic of an embodiment of the present invention is illustrated in FIG. 1. This embodiment preferably comprises a portable optical spectroscopy apparatus for measurement of gas concentration. The apparatus is preferably a handheld device. The optical spectroscopy apparatus preferably comprises laser light source 10 and a fixed length optical path which receives light from laser light source 10. The fixed length optical path contains a gas to be detected and preferably comprises multiple pass optical cell 20. The gas to be detected is preferably pumped continuously through multiple pass optical cell 20 using a pump. Detector 120 preferably receives light at an end of the fixed length optical path, after the light passes through the gas to be detected. Detector 120 is connected to signal processing electronics 30. Signal processing electronics 30 determines one or more gas concentrations. Microcontroller 40 preferably receives the concentration data from signal processing electronics 30, and displays the concentration data using display 70. Display 70 can preferably display the gas concentration data in PPM, percent LEL and/or percent gas. This embodiment also preferably comprises a reference signal for linelocking and comparing signal sources. To establish a reference signal, this embodiment preferably comprises beamsplitter 100, sample container 80 containing the gas, and detector 110 for receiving light from sample container 80. Detector 110 is connected to signal processing electronics 30 which determines concentration of the reference signal based on the amount of light detector 110 detects. Sample container 80 preferably comprises approximately a methane mixture with an optical absorbance of 0.001-0.1.

In another embodiment of the present invention, a diode laser sensor measures an optical absorption for a methane concentration. The optical absorption is preferably at a wavelength corresponding to a methane absorption line between 1630 and 1700 nm. At the specified wavelength, methane has a very narrow absorbance where there are typically no interfering species to absorb. A high sensitivity optical absorption technique known as wavelength modulation spectroscopy and an enclosed multiple pass optical cell are preferably used to obtain sub-ppm sensitivity. At higher concentrations, where the optical absorption becomes thick, conventional absorption spectroscopy is preferably used. In this embodiment, the methane is continuously drawn through the multiple pass optical cell with a small pump.

In yet another embodiment of the present invention, laser 10 is preferably a diode laser. Laser 10 characteristics preferably comprise approximately 0.1-5 mW output power, approximately 5-150 mA diode injection current, and approximately 0.5-3 V diode drop. Laser 10 is preferably mounted directly on a miniature thermoelectric cooler in a T05 can, which allows for thermal control while minimizing power consumption. Multiple pass optical cell 20 preferably comprises two mirrors 21, 21' configured in a Herriott cell design. This design makes the system insensitive to mechanical vibration. More preferably, the base path of multiple pass optical cell 20 is approximately 5-20 cm and the total fixed length optical path provided by multiple pass optical cell 20 is approximately 50-500 cm. In this embodiment, multiple pass optical cell 20 volume is approximately 10-50 ml. The pumping speed through multiple pass optical cell 20 is approximately 5-50 ml/sec. In an embodiment of the present invention, a portion of the laser beam is split off via beamsplitter 100 prior to entering multiple pass optical cell 20 to form a reference beam. The sample and reference beams are preferably detected using a semiconductor detector. More preferably, the beams are detected with an indium gallium arsende (InGaAs) detector. Most preferably, the beams are detected using an approximately 1 mm diameter, 1.9 μm extended wavelength InGaAs detector.

Below concentrations of approximately 1000 ppm, wavelength modulation spectroscopy is preferably employed. Absorbances from approximately $10^{-1}$ to $10^{-5}$ are routinely measurable in a one second period with this technique. The high sensitivity is obtained by conducting spectral measurements at a frequency high enough to greatly reduce laser excess noise. The technique is implemented by rapidly modulating the laser wavelength and performing phase sensitive photodetection at a harmonic of the modulation frequency. Since a diode laser's wavelength tunes with injection current, a small periodic oscillation of the diode laser current results in wavelength modulation. The gas absorption converts the wavelength modulation to an amplitude modulation of the transmitted beam. A relatively slow sweep of the laser wavelength (current) across the spectral region generates a spectrum. The spectrum resulting from $n^{th}$ harmonic detection appears as the $n^{th}$ derivative of the unmodulated absorbance. In the sensor, second harmonic detection is preferably used.

Because diode lasers are generally linear in intensity versus wavelength, second harmonic detection has the added benefit of being a zero baseline measurement. The amplitude of the spectral peak is proportional to absorbance and thus, through Beer's law, proportional to concentration. The peak amplitude is also linear with respect to the beam intensity. Thus, signals are normalized by the light intensity. At concentrations above approximately 1000 ppm, the laser modulation is turned off and conventional absorbance spectroscopy is used. At gas concentrations greater than about 10%, the sample becomes optically thick. In this region, a modified form of absorbance spectroscopy is performed.

In an embodiment of the present invention, digital signal processor (DSP) based electronics system performs optical system control and data acquisition. The power consumption of this electronics system is approximately 0.5-0.8 W. The component costs excluding detectors are about $250 in single quantities and the board size is approximately 2–10×10–30 cm. DSP can preferably perform about 100 million instructions/second, require only approximately 150-500 mW of power, and costs about $10. The system controls laser temperature and has laser current resolution of approximately 0.1-1.0 µA. Laser modulation is performed at approximately 10-1000 kHz and phase controlled lock-in detection at twice the modulation frequency. The DSP system of this embodiment has at least two lock-in amplifier detectors 110 and 120, one for the sample beam and one for the reference beam. Methane spectra are generated by stepping the laser current through a 100 point ramp every msec. Gain control of the signal is preferably performed three times a second in order to keep analog signal levels constant. Sample spectra are digitized and fit with the actively measured reference spectra using singular value decomposition analysis. This fitting is also performed approximately three times a second. The averaged result is reported to microcontroller 40 approximately once a second. A pressure gage and thermistor are preferably used to monitor the sample pressure and temperature.

In one embodiment of the present invention, microcontroller 40 takes DSP 30 serial outputs, applies stored calibration constants to the raw readings, and displays the results on display 70. Display 70 is preferably a liquid crystal display. More preferably, display 70 is an approximately 1×16 liquid crystal display. Microcontroller 40 preferably has a compact flash card on which it records calibrations and any other needed information. User button 60 allows a user to answer yes/no questions regarding instrument options and modes. This embodiment preferably comprises alarms 50 that are controlled by microcontroller 40 preferably include an audible alarm, a vibrating buzzer, an LED, and an audio headset alarm.

An embodiment of the present invention comprises a casing around the instrument. The casing is preferably plastic. An inlet tube is preferably used as a sample probe. More preferably a telescoping inlet tube is used as a sample probe. Most preferably, a telescoping inlet tube with a 5 micron filter attached near the input is used as a sample probe. The sample probe preferably connects to multiple pass optical cell 20. In normal leak surveying, the end of the probe is dragged along the ground. A rigid probe can optionally be attached to the sample probe for detection of gases underground. The rigid probe enables a user to easily detect gases underground. The present invention requires only single-handed operation when used in this manner. A clogged filter warning is provided when the inlet pressure drops significantly below ambient pressure. The invention preferably runs using a wireless energy source, such as batteries. More preferably, the present invention runs on four AA size rechargeable nickel metal hydride batteries. The invention can run for approximately 14 hours on one charge. When the rechargeable batteries run out, the present invention can be set to run on an alternate nonrechargeable battery source. For example, four disposable AA lithium batteries will run the invention for approximately 8 hours. Total power consumption of the invention is preferably under about 2 watts. Alarming or use of the LCD backlight consumes additional power.

In one embodiment of the present invention, a calibration, preferably a two point calibration, performed by a user in order to establish span and offset factors. In this embodiment, one calibration point is performed on clean air. The other calibration point is performed on approximately 1000 ppm methane mixture in air or nitrogen. The calibration mixture is introduced into the instrument using a demand flow regulator. A demand flow regulator feeds gas to the system at the pumping speed, thereby keeping the sample pressure from changing. The calibration is performed in both wavelength modulation and normal absorbance modes. Calibration can be performed as little as once a month.

Industrial Applicability:

The invention is further illustrated by the following non-limiting examples.

EXAMPLE 1

Instrument performance was assessed in regard to a number of parameters including accuracy, precision, and response and recovery times. However, an insightful and fundamental test was conducted to see how the invention performed in the field environment compared to standard instrumentation used for the application. Thus, the performance of the invention was compared to that of the Southern Cross Corp. Flame Pack 400 in a controlled leak field. The Flame Pack is a flame ionization instrument commonly used for leak surveying. Walking surveys were conducted simultaneously with both instruments. The invention was found to be equally adept in finding low ppm leak plumes as the flame ionization instrument. The baseline was a steady zero ppm in clean air (the reading is relative to ambient methane) and did not false alarm. The response time of the invention was one second faster than flame ionization instrument. Since absorption spectra are collected at 1 kHz, the invention's response was limited by the pumping speed through multiple pass optical cell 20.

Recovery of the invention from exposure to gas was measured on four units. Calibrated gas mixtures were introduced into the invention from pressurized cylinders with a demand flow regulator. Gas mixtures from 1 ppm to pure gas were used. The recovery times back to zero ppm are shown in FIG. 2. The times vary from 2 seconds when exposed to 1 ppm to 60 seconds when exposed to pure gas. With 100% gas, the invention dropped to 20-30 ppm within 15 sec and then cleared out more slowly. Outgassing or trapped residual gas were the likely cause of the recovery slowdown. In comparison, standard instruments require several minutes to recover from high gas exposure.

Precision measurements were made at each order of magnitude from 10 ppm to pure gas. Each measurement recorded the one second output from the unit over a time period of 10 min.

Figure 3:
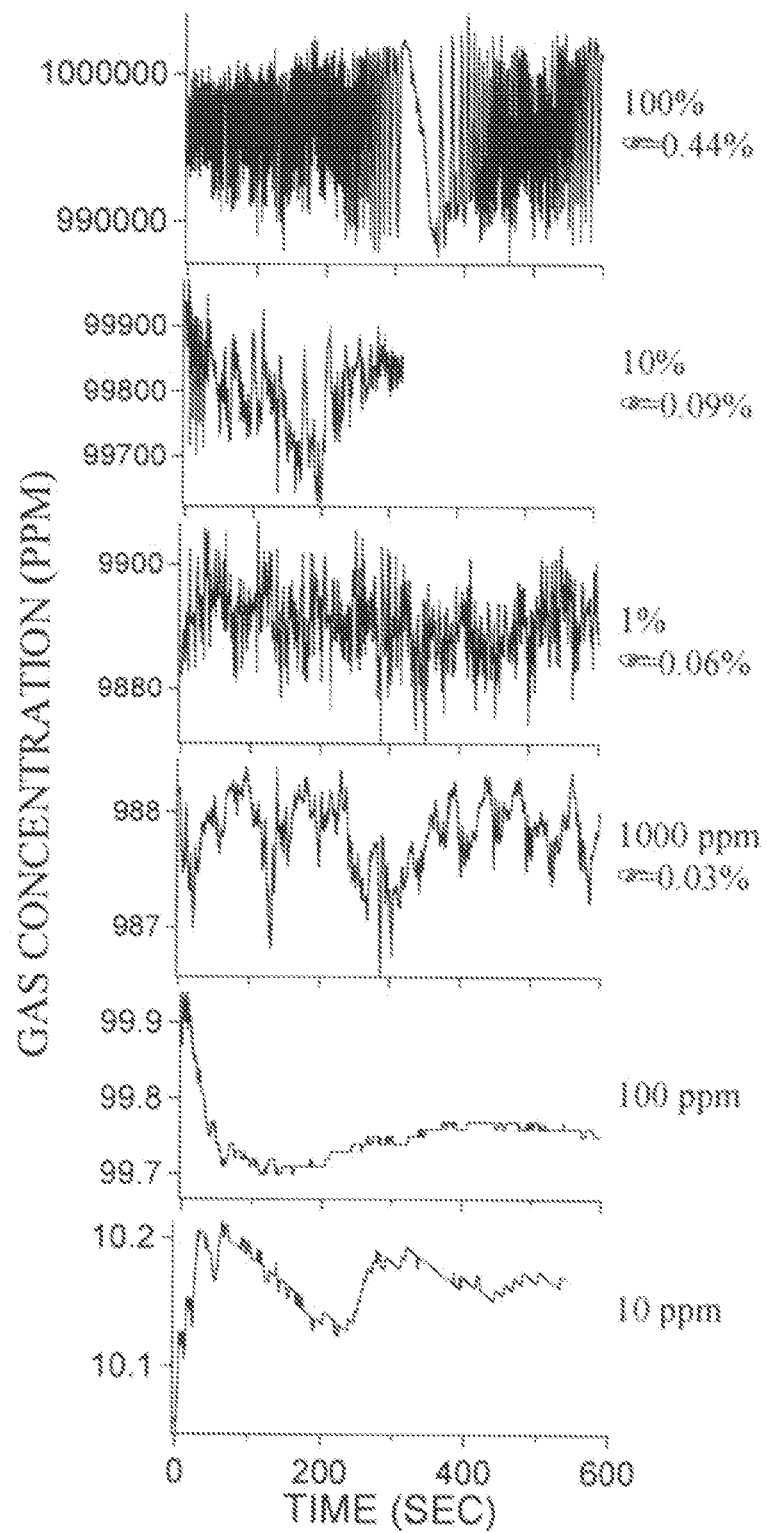
FIG. 3 is a chart showing data for each measured gas concentration using the preferred embodiment.

The invention software was altered for these measurements to provide increased digital readout resolution. FIG. 3 shows the data for each measured gas concentration. The one standard deviation precision was observed to be no worse than 0.4% of the reading at any gas level. At 1000 ppm, the precision was 0.03%.

Since the readout was programmed for field use to round up to the nearest integer value, the accuracy evaluation was often limited by round off error. A more accurate assessment required a software alteration to display higher precision as was done in the precision testing. Results are shown in FIG. 4. The greatest accuracy in terms of reading percentage was observed at the 1% gas level. The readings at this concentration were less than the 0.05% gas concentration resolution displayed by the readout. The high gas readings were the least accurate with an error of 2% gas. The 100 ppm readings which are least affected by the digital readout resolution show an accuracy of 5 ppm. The trace ppm readings were accurate to approximately 1 ppm.

Results

The present invention has been designed for natural gas leak inspection surveying. With its faster response and much faster recovery time, the invention surpassed the industry standard instrument in detecting leaks in field tests. Preliminary accuracy measurements show that the invention was very accurate in the lower explosion limit range (0.5-5% gas), the decision point range for taking corrective action regarding the leak source. Sensor precision was observed to be better than 1% and is far beyond the requirement for this application. Recovery from high gas exposure is much faster than standard instruments. In addition, the invention is lighter (approximately 3 pounds) and does not require consumables. It is also safer then industry standard instruments for the fire hazardous environment in which it operates. The ability of the invention to measure the ppm to pure gas range makes it suitable to replace standard instruments which have limited dynamic ranges.

Leak detection is an ideal application for the present invention. While wavelength modulation diode laser sensing fulfills the requirements for high sensitivity, large dynamic range, selectivity, and fast time response, the operational nature of a measurement that is mostly measuring a zero baseline is well suited to it. Calibration span is very stable for wavelength modulation measurements. However, offset drift in the high sensitivity range corresponding to absorbances in the low $10^{-5}$ range typically limits accuracy. Since the invention frequently measures zero concentration gas, offset corrections can be implemented quickly enough in software to eliminate slow instrument drift. The laser sensor baseline then becomes quite stable for this application, improving accuracy.

The present invention is handheld (preferably 12 inches by 6 inches) and can seamlessly switch between PPM, LEL % and % Gas in seconds and has an easy one button operation. In addition, the invention can also be used as a combustible gas indicator. It meets ISO 9002 Standards. Calibration data retrieved from the invention can be downloaded to a spreadsheet application, such as Excel.

The performance, physical specifications, and pricing levels of this invention leads to its use in other applications, other than the ones discussed herein and for other gases. For example, switching to a 1.5 μm laser will allow ammonia detection. Ammonia leak detection is important in large warehouse refrigeration systems. Other gases that can be detected with near infrared diode lasers include hydrogen fluoride, hydrogen chloride, hydrogen cyanide, carbon dioxide, and water vapor. Slight modifications to the multiple pass optical cell 20 can decrease or increase the optical pathlength to change system sensitivity. The basic electronics remain the same.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A portable optical spectroscopy apparatus for measurement of gas concentration, said apparatus comprising:
    a laser light source;
    a fixed length optical path receiving light from said source and containing a gas to be detected;
    a beamsplitter, a sample container containing the gas, a detector receiving light from the sample container, and signal-processing electronics establishing linelockinq and a comparative signal source of said absorption feature;
    a detector receiving light at an end of said path;
    signal processing electronics acquiring data from said detector; and
    a microcontroller receiving said data from said signal processing electronics;
    wherein said apparatus is handheld.

2. The apparatus of claim 1 wherein said path comprises a multiple pass optical cell.

3. The apparatus of claim 2 further comprising a pump that continuously pumps said gas through said cell.

4. The apparatus of claim 2 wherein said cell comprises two mirrors configured in a Herriott cell design.

5. The apparatus of claim 1 wherein said source comprises a diode laser.

6. The apparatus of claim 1 additionally comprising a display for displaying said data from said microcontroller.

7. The apparatus of claim 6 wherein said display can switch between displaying said data in PPM, percent LEL and percent gas.

8. The apparatus of claim 1 additionally comprising alarms controlled by said microcontroller.

9. The apparatus of claim 1 wherein said gas is methane.

10. The apparatus of claim 1 further comprising a user button for inputting options and modes.

11. The apparatus of claim 1 further comprising a telescoping sample probe.

12. The apparatus of claim 1 further comprising batteries.

13. The apparatus of claim 1 wherein said apparatus can be held with a single hand.

14. The apparatus of claim 1 further comprising a rigid probe for measurement of underground gas concentrations.

15. A portable optical spectroscopy method for measurement of gas concentration, the method comprising the steps of:
    holding a portable optical spectroscopy apparatus in an area to be measured;
    emitting light from a laser light source attached to the apparatus;
    receiving light via a fixed length optical path from the source and containing a gas to be detected;
    employing a beamsplitter, a sample container containing the gas, a detector receiving light from the sample container, and signal-processing electronics to establish linelockinq and a comparative signal source of the absorption feature;
    receiving light via the detector at an end of the path;
    determining one or more gas concentrations via signal processing electronics connected to the detector; and
    reporting the gas concentration data to a microcontroller.

16. The method of claim 15 wherein said source comprises a diode laser.

17. The method of claim 15 wherein the path comprises a multiple pass optical cell.

18. The method of claim 17 additionally comprising continuously pumping the gas to be detected through the cell.

19. The method of claim 17 wherein the cell comprises two mirrors configured in a Herriott cell design.

20. The method of claim 15 additionally comprising displaying the gas concentration data.

21. The method of claim 15 additionally comprising controlling alarms via the microcontroller.

22. The method of claim 15 additionally comprising performing a calibration.

23. The method of claim 15 wherein the gas is methane.

24. The method of claim 15 additionally comprising inputting options and modes via a user button.

25. The method of claim 15 additionally comprising telescoping a sample probe in the area to be measured.

26. The method of claim 15 additionally comprising powering the apparatus with batteries.

27. The method of claim 15 wherein the holding step is performed with a single hand.

* * * * *